(12) United States Patent
Liang et al.

(10) Patent No.: US 11,511,006 B2
(45) Date of Patent: Nov. 29, 2022

(54) LED ULTRAVIOLET GERMICIDAL LAMP

(71) Applicant: MICROCOOL ENTERPRISE INC, Cerritos, CA (US)

(72) Inventors: Zhigang Liang, Changsha (CN); Bing Li, Changsha (CN)

(73) Assignee: MICROCOOL ENTERPRISE INC, Cerritos, CA (US)

( * ) Notice: Subject to any disclaimer, the term of this patent is extended or adjusted under 35 U.S.C. 154(b) by 215 days.

(21) Appl. No.: 16/885,374

(22) Filed: May 28, 2020

(65) Prior Publication Data

US 2021/0275701 A1 Sep. 9, 2021

(30) Foreign Application Priority Data

Mar. 9, 2020 (CN) .......................... 202020276856.2

(51) Int. Cl.
| | | |
|---|---|---|
| A61L 2/10 | (2006.01) | |
| A61L 2/08 | (2006.01) | |
| B01J 21/06 | (2006.01) | |
| B01J 35/00 | (2006.01) | |
| A61L 2/26 | (2006.01) | |

(52) U.S. Cl.
CPC ................. *A61L 2/10* (2013.01); *A61L 2/088* (2013.01); *A61L 2/26* (2013.01); *B01J 21/063* (2013.01); *B01J 35/004* (2013.01); *A61L 2202/11* (2013.01)

(58) Field of Classification Search
CPC . A61L 2/10; A61L 2/088; A61L 9/205; F21V 49/74; F21S 8/06; C03F 2201/3221; C03F 2201/3222
See application file for complete search history.

(56) References Cited

U.S. PATENT DOCUMENTS

| 2018/0372309 A1* | 12/2018 | Lou ...................... F21V 29/508 |
| 2020/0282098 A1* | 9/2020 | Anderson .............. B01J 35/004 |

(Continued)

FOREIGN PATENT DOCUMENTS

CN 209893255 U * 1/2020

OTHER PUBLICATIONS

Ahmad et al., 'History of UV Lamps, Types, and Their Applications', 2017, Ultraviolet Light in Human Health, Diseases and Environment, Advances in Experimental Medicine and Biology 996 (pp. 3-11) (Year: 2017).*

(Continued)

*Primary Examiner* — Eliza W Osenbaugh-Stewart
(74) *Attorney, Agent, or Firm* — Bayramoglu Law Offices LLC

(57) ABSTRACT

A LED ultraviolet germicidal lamp includes a bracket, a power box, a driving light source, a heat sink, an ultraviolet light source, a lampshade, a quartz glass, a catalyst gauze, and a lamp frame. The bracket is connected to the heat sink, and the power box and the driving light source are provided in the bracket in sequence from outside to inside. The driving light source is provided in the power box and is connected to the power box by bolts. The heat sink is connected to the power box and is provided at a lower end of the power box. Titanium dioxide is used as the catalyst and is catalyzed by the UVC light source. Hydroxyl radicals produced when nanoscale titanium dioxide catalyst gauze is exposed to the UVC light source destroy bacteria and viruses.

17 Claims, 3 Drawing Sheets

(56) References Cited

U.S. PATENT DOCUMENTS

2021/0170061 A1* 6/2021 Kim .................. B01J 37/26
2022/0193280 A1* 6/2022 James ................. A61L 2/10

OTHER PUBLICATIONS

Gerdes et al. 'UV C Luminescence of a modified zirconium silicate framework upon cathode ray and UVU excitation', Mar. 5, 2018, Journal of Luminescence 198 pp. 410-417 (Year: 2018).*

* cited by examiner

LED ULTRAVIOLET GERMICIDAL LAMP

CROSS REFERENCE TO THE RELATED APPLICATIOS

This application is based upon and claims priority to Chinese Patent Application No. 202020276856.2, filed on Mar. 9, 2020, the entire contents of which are incorporated herein by reference.

TECHNICAL FIELD

The present invention relates to the technical field of sterilization, and more specifically, relates to a light emitting diode (LED) ultraviolet germicidal lamp.

BACKGROUND

Photocatalysis using ultraviolet (UV) light has been applied in sterilization for several decades. Due to the complexity of the technique and the heat dissipation of the chip, however, it is difficult to increase the power of ultraviolet light sources. Another problem that limits the use of the technique is the difficulty in expanding the heat dissipation area. Recent advancements addressing heat dissipation of the chip have resulted in the photocatalytic sterilization technique with UV light replacing traditional chlorination disinfection in some applications. Photocatalytic sterilization is now a preferred means for eradicating unwanted micro-organisms and has proven especially efficacious in ridding the working space of viruses and bacteria. As the mechanism of UV disinfection becomes better understood, new UV techniques are advanced, and the designs of disinfection devices increase, UV disinfection is expected to supplant traditional chlorination disinfection.

SUMMARY

For the above problems, the present invention provides a LED ultraviolet germicidal lamp with an adjustable angle and using titanium dioxide as a catalyst.

To achieve the above objective, the present invention provides a LED ultraviolet germicidal lamp, including a bracket, a power box, a driving light source, a heat sink, an ultraviolet light source, a lampshade, a quartz glass, a catalyst gauze, and a lamp frame.

The bracket is connected to the heat sink, and the power box and the driving light source are provided in the bracket in sequence from outside to inside.

The driving light source is provided in the power box and is connected to the power box by bolts.

The heat sink is connected to the power box and is provided at the lower end of the power box.

The ultraviolet light source is connected to the heat sink and is provided at the lower end of the heat sink.

The lampshade is connected to the lower end of the heat sink and is provided on the ultraviolet light source.

The quartz glass, the catalyst gauze and the lamp frame are arranged at the lower end of the lampshade in sequence, and are fixed by clamping blocks provided on the lampshade.

Preferably, the driving light source is a surface-mounted-device (SMD) LED light source or/and a chip-on-board (COB) light source, wherein chips of the SMD LED light source are packaged collectively.

Preferably, the ultraviolet light source is an ultraviolet C (UVC) light source.

Preferably, the catalyst gauze is a nanoscale titanium dioxide catalyst gauze made of a nanoscale titanium dioxide material.

As a further solution of the present invention, the heat sink includes a heat sink and heat sinking fins radially arranged on the outer circumference of the heat sink, and each of the heat sinking fins is substantially saw-toothed, and protrusions are provided on both sides of each of the heat sinking fins.

Preferably, the thickness of each of the heat sinking fins is 1-2 mm, the cross section of each of the protrusions is semicircular, triangular, rectangular, etc., and the height of each of the protrusions is 0.5-1.5 mm.

As a further solution of the present invention, in order to realize the angle adjustment of the ultraviolet light source, the bracket further includes a plurality of bracket fixing seats fixed on the bracket, and each of the bracket fixing seats is provided with a waist-shaped hole for facilitating the installation of screws, so that the angles between the bracket and the heat sink are modified by adjusting different positions of the screws between the bracket and the heat sink in the waist-shaped hole.

As a further solution of the present invention, in order to effectively prevent the water fog produced by the working of LED the ultraviolet germicidal lamp from infiltrating into the LED ultraviolet germicidal lamp from the lamp frame, a sealing groove is fixedly provided between the lamp frame and the lampshade.

The technical solutions of the present invention have the following advantages:

1. The present invention has a simple structure, convenient use and wide applicability.

2. In the present invention, the irradiation angle of the ultraviolet light source is adjustable, which effectively broadens the application range of the present invention.

3. In the present invention, the SMD LED light source with chips packaged collectively or/and the COB light source are used as the driving light source, so that the present invention has the characteristics of good disinfection effectivity, long service life, and high sterilization efficiency, and the advantages of strong disinfection ability without pollution.

4. In the present invention, titanium dioxide is used as the catalyst and is catalyzed by the UVC light source. The germs are eradicated by the hydroxyl radicals produced by catalyzing the nanoscale titanium dioxide catalyst gauze with the UVC light source. Therefore, in an effectively sealed space, the hydroxyl free radicals produced by the photocatalysis absorb the light having greater energy than a forbidden band width (about 3.2 eV) thereof when irradiated by the ultraviolet light, so that the electrons in the valence band are excited to the conduction band. Due to a lack of electrons, the valence electron band forms electron holes, thereby forming an electron-hole pair that is easy to move and has strong activity. On one hand, the electron-hole pair can recombine with each other when various redox reactions occur, thereby releasing energy in the form of heat or fluorescence; on the other hand, the electron-hole pair can be dissociated into free holes and free electrons that migrate freely to the lattice surface or other reaction sites in the lattice, and the free holes and free electrons are immediately captured by the surface groups. Meanwhile, the surface hydroxyl groups generated by the water activation on the surface of the titanium dioxide catalyst gauze capture free holes to form the hydroxyl free radicals, so the dissociative free electrons quickly combine with absorbed oxygen to produce superoxide free radicals to kill the surrounding bacteria and viruses, thereby achieving the broad-range sterilization.

In addition to the applications, characteristics and advantages described above, the present invention has other applications, characteristics and advantages. The present invention is further illuminated in detail with reference to the drawings below.

BRIEF DESCRIPTION OF THE DRAWINGS

To more clearly illustrate the technical solutions in the embodiments of the present disclosure or the prior art, the drawings that need to be used in the description of the embodiments or the prior art are briefly introduced. Obviously, the drawings described below are merely the embodiments in the present disclosure, and for those skilled in the art, other drawings can be obtained according to these drawings without creative work.

In the figures,

1: bracket, 1-1: bracket holder, 2: power box, 3: driving light source, 4: heat sink, 4-1: heat sinking fin, 4-2: sawtooth, 4-3: protrusion, 5: UVC light source, 6: lampshade, 7: quartz glass, 8: nanoscale titanium dioxide catalyst gauze, and 9: lamp frame.

DETAILED DESCRIPTION OF THE EMBODIMENTS

The embodiments of the present invention are described in detail below, and the present invention includes other embodiments in the scope of the limitations of the claims in the present disclosure.

Figure 1:
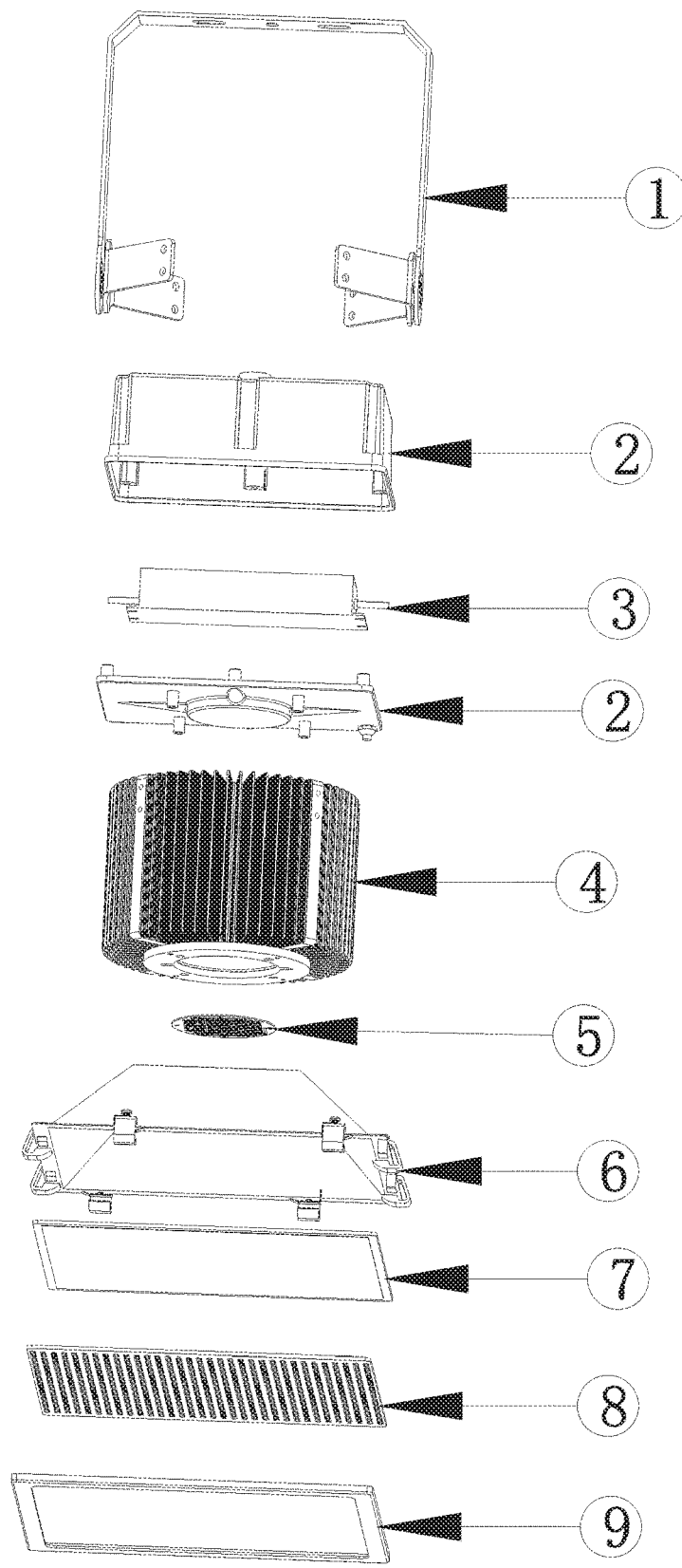
FIG. 1 is an exploded view showing the present invention.
Figure 2:
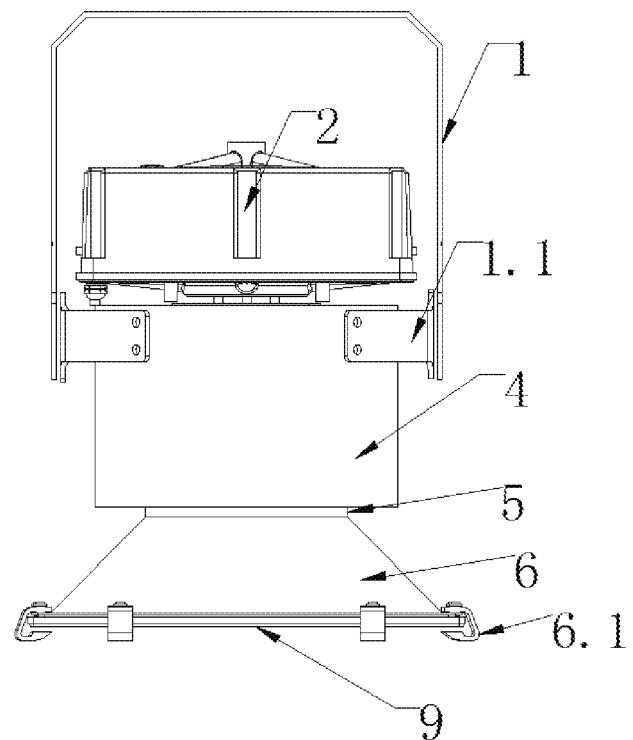
FIG. 2 is a front view showing the present invention.
Figure 3:
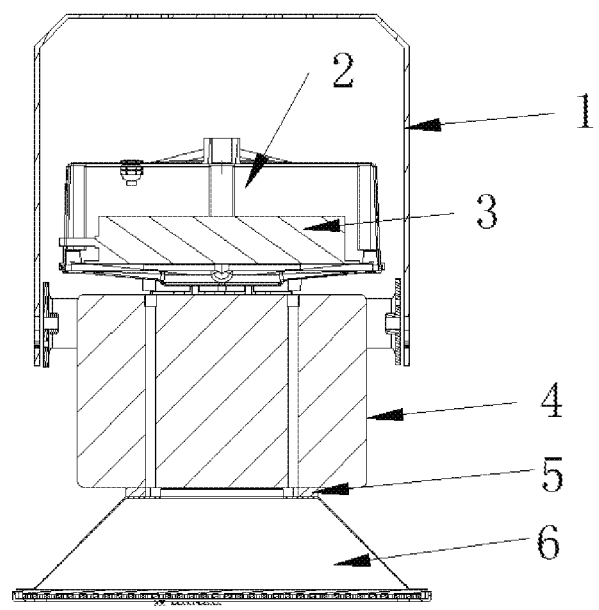
FIG. 3 is a sectional view of the front view of the present invention.

As shown in FIGS. 1-3, the present invention provides a LED ultraviolet germicidal lamp, including the bracket 1, the power box 2, the driving light source 3, the heat sink 4, the UVC light source 5, the lampshade 6, the quartz glass 7, the nanoscale titanium dioxide catalyst gauze 8, and the lamp frame 9.

The power box 2 and the driving light source 3 are arranged in the bracket 1 in sequence, and the driving light source 3 is a LED light source and is fixedly mounted in the power box 2 by bolts.

The heat sink 4 is connected to the power box 2 by bolts and is fixedly provided at the lower end of the power box 2.

The UVC light source 5 is connected to the heat sink 4 by bolts and is fixedly provided at the lower end of the heat sink 4.

The lampshade 6 is connected to the heat sink 4 by bolts, is fixedly provided at the lower end of the heat sink 4, and is sleeved on the UVC light source 5.

The quartz glass 7, the nanoscale titanium dioxide catalyst gauze 8 and the lamp frame 9 are arranged at the lower end of the lampshade 6 in sequence and are fixed by a plurality of clamping blocks 6-1 provided on the lampshade 6.

As a preferred embodiment of the present invention, the bracket 1 further includes a plurality of bracket fixing seats 1-1 fixedly provided on the bracket 1, and each of the bracket fixing seats 1-1 is provided with a plurality of waist-shaped holes configured for installation of screws. The screws in the waist-shaped holes are adjusted to different positions between the bracket fixing seats 1-1 and the heat sink 4, so as to modify the angles between the bracket 1 and the heat sink 4, thereby realizing the angle adjustment of the UVC light source 5.

As a preferred embodiment of the present invention, the lamp frame 9 is provided with a sealing groove for installing a sealing ring (not shown in the drawing) provided between the lamp frame 9 and the lampshade 6, so as to effectively prevent the infiltration of water mist from the lamp frame 9.

As a preferred embodiment of the present invention, the driving light source 3 is a surface-mounted-device (SMD) LED light source or/and a chip-on-board (COB) light source, wherein chips of the SMD LED light source are packaged collectively.

Figure 4:
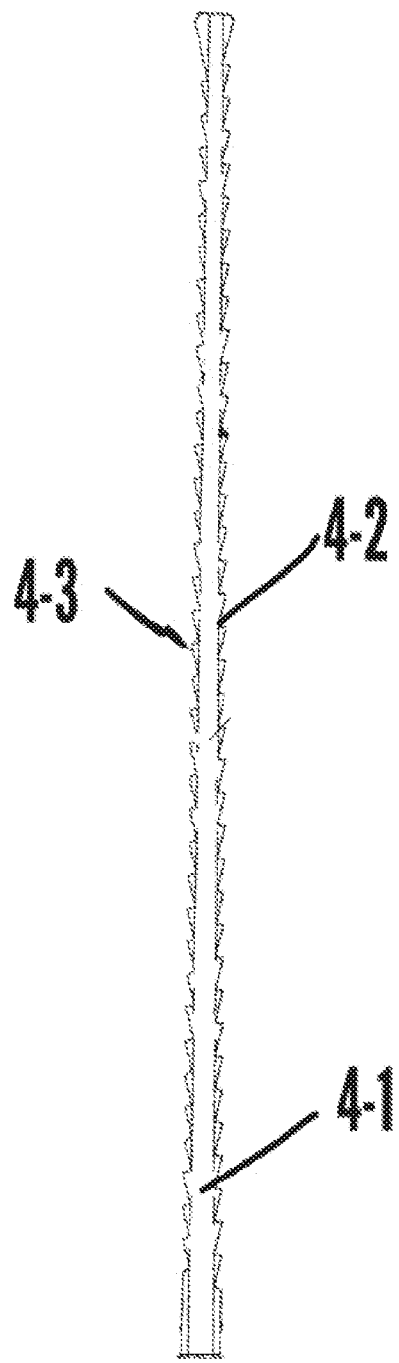
FIG. 4 is a schematic diagram showing a section of a heat sinking fin of the present invention along the width direction.

As a further embodiment of the present invention, as shown in FIG. 4, the heat sink 4 includes the heat sink and the heat sinking fins 4-1 radially provided on the outer circumference of the heat sink. A plurality of sawteeth 4-2 are provided on one side of the cross section of the heat sinking fins 4-1 along its width direction, which is configured to conduct heat to the heat sinking fin 4-1 and then dissipate heat by air convection. A plurality of protrusions 4-3 are provided on the other side of the cross section along the width direction of the heat sinking fin 4-1, which is configured to increase the heat dissipation area of the heat sinking fin 4-1 and improves the heat dissipation efficiency of the heat sink 4.

Preferably, the thickness T of the heat sinking fin 4-1 is 1-2 mm;

Preferably, the cross section of the protrusion 4-3 is semicircular, triangular, rectangular, etc., and the height H of the protrusion 4-3 is 0.5-1.5 mm.

The working principle of the present invention is as follows.

In the present invention, titanium dioxide is used as the catalyst and is catalyzed by a UVC light source. The hydroxyl radicals produced by catalyzing the nanoscale titanium dioxide catalyst gauze with the UVC light source are configured to eradicate bacteria and viruses.

The above are only the preferred embodiments of the present invention and are not used to limit the present invention. For those skilled in the art, various changes and modification can be made according to the present invention. Any modification, equivalent replacement, improvement, etc. made within the spirit and principles of the present invention shall fall in the protection scope of the present invention.

What is claimed is:

1. An ultraviolet germicidal lamp, comprising a bracket, a power box, a heat sink, an ultraviolet light source, a lampshade, a quartz glass, a catalyst gauze, and a lamp frame; wherein the bracket is connected to the heat sink, and the power box is provided in the bracket;

the heat sink is connected to the power box and is provided at a lower end of the power box;

the ultraviolet light source is connected to the heat sink and is provided at a lower end of the heat sink;

the lampshade is connected to the lower end of the heat sink and is sleeved on the ultraviolet light source; and the quartz glass, the catalyst gauze and the lamp frame are arranged at a lower end of the lampshade in sequence, and are fixed by clamping blocks provided on the lampshade.

2. The ultraviolet germicidal lamp according to claim 1, wherein the ultraviolet light source is an ultraviolet C (UVC) light source.

3. The ultraviolet germicidal lamp according to claim 2, wherein the bracket further comprises a plurality of bracket fixing seats fixed on the bracket, and each of the bracket fixing seats is provided with a waist-shaped hole for installation of screws.

4. The ultraviolet germicidal lamp according to claim 2, wherein a sealing groove is fixedly provided between the lamp frame and the lampshade.

5. The ultraviolet germicidal lamp according to claim 1, wherein the catalyst gauze is a nanoscale titanium dioxide catalyst gauze made of a nanoscale titanium dioxide material.

6. The ultraviolet germicidal lamp according to claim 5, wherein the bracket further comprises a plurality of bracket fixing seats fixed on the bracket, and each of the bracket fixing seats is provided with a waist-shaped hole for installation of screws.

7. The ultraviolet germicidal lamp according to claim 5, wherein a sealing groove is fixedly provided between the lamp frame and the lampshade.

8. The ultraviolet germicidal lamp according to claim 1, wherein the heat sink comprises a heat sink and heat sinking fins radially arranged on an outer circumference of the heat sink, each of the heat sinking fins is substantially saw-toothed, and protrusions are provided on both sides of each of the heat sinking fins.

9. The ultraviolet germicidal lamp according to claim 8, wherein a thickness of each of the heat sinking fins is 1-2 mm.

10. The ultraviolet germicidal lamp according to claim 9, wherein the bracket further comprises a plurality of bracket fixing seats fixed on the bracket, and each of the bracket fixing seats is provided with a waist-shaped hole for installation of screws.

11. The ultraviolet germicidal lamp according to claim 9, wherein a sealing groove is fixedly provided between the lamp frame and the lampshade.

12. The ultraviolet germicidal lamp according to claim 8, wherein a cross section of each of the protrusions is semi-circular, triangular or rectangular, and a height of each of the protrusions is 0.5-1.5 mm.

13. The ultraviolet germicidal lamp according to claim 12, wherein the bracket further comprises a plurality of bracket fixing seats fixed on the bracket, and each of the bracket fixing seats is provided with a waist-shaped hole for installation of screws.

14. The ultraviolet germicidal lamp according to claim 8, wherein the bracket further comprises a plurality of bracket fixing seats fixed on the bracket, and each of the bracket fixing seats is provided with a waist-shaped hole for installation of screws.

15. The ultraviolet germicidal lamp according to claim 8, wherein a sealing groove is fixedly provided between the lamp frame and the lampshade.

16. The ultraviolet germicidal lamp according to claim 1, wherein the bracket further comprises a plurality of bracket fixing seats fixed on the bracket, and each of the bracket fixing seats is provided with a waist-shaped hole for installation of screws.

17. The ultraviolet germicidal lamp according to claim 1, wherein a sealing groove is fixedly provided between the lamp frame and the lampshade.

* * * * *